United States Patent [19]

Henegar et al.

[11] Patent Number: 5,389,669
[45] Date of Patent: Feb. 14, 1995

[54] PYRROLE THIOCARBOXAMIDE INSECTICIDAL AND ACARICIDAL AGENTS

[75] Inventors: Kevin E. Henegar, Portage, Mich.; Roger W. Addor, Pennington, N.J.

[73] Assignee: American Cyanamid Company, Wayne, N.J.

[21] Appl. No.: 150,626

[22] Filed: Nov. 10, 1993

Related U.S. Application Data

[62] Division of Ser. No. 971,025, Nov. 3, 1992, Pat. No. 5,286,742.

[51] Int. Cl.$^6$ .................. A01N 43/36; A01N 55/00
[52] U.S. Cl. ...................... 514/423; 514/63; 514/422
[58] Field of Search .................... 514/423, 422, 63

[56] References Cited

U.S. PATENT DOCUMENTS

| | | | |
|---|---|---|---|
| 3,393,201 | 7/1968 | Préau | 260/326.3 |
| 5,157,047 | 10/1992 | Kameswaran et al. | 514/423 |

*Primary Examiner*—Allen J. Robinson
*Attorney, Agent, or Firm*—Michael P. Morris

[57] ABSTRACT

There are provided pyrrole thiocarboxamide compounds which are useful for the control of insects and acarina. Further provided are compositions and methods comprising those compounds for the protection of plants from attack by insects and acarina.

10 Claims, No Drawings

PYRROLE THIOCARBOXAMIDE INSECTICIDAL AND ACARICIDAL AGENTS

This is a divisional of application Ser. No. 07/971,025, filed on Nov. 3, 1992, now U.S. Pat. No. 5,286,742.

BACKGROUND OF THE INVENTION

Insects and acarina destroy growing and harvested crops. In the United States alone, agronomic crops must compete with thousands of insect and acarid species. In particular, tobacco budworms, southern armyworms and two-spotted spider mites are especially devastating to crops.

In spite of the commercial insecticides and acaricides available today, damage to crops, both growing and harvested, caused by insects and acarina still occurs. Accordingly, there is ongoing research to create new and more effective insecticides and acaricides.

Certain pyrrole compounds are known to possess insecticidal and acaricidal activity (see, e.g., U.S. Pat. No. 5,010,098 and U.S. Pat. application Ser. Nos. 600,054 filed on Oct. 18, 1990; 621,162 filed on Nov. 30, 1990; 795,407 filed on Nov. 20, 1991; and 803,289 filed on Dec. 4, 1991). However, none of the pyrroles disclosed in those patent applications are within the scope of the present invention.

It is therefore an object of the present invention to provide pyrrole thiocarboxamide compounds which are highly effective for controlling insects and acarina.

It is also an object of the present invention to provide a method for protecting growing plants from attack by insects and acarina by applying to the foliage of said plants or to the soil or water in which they are growing an insecticidally or acaricidally effective amount of a pyrrole thiocarboxamide compound.

These and other objects of the present invention will become more apparent from the detailed description thereof set forth below.

SUMMARY OF THE INVENTION

The present invention describes pyrrole thiocarboxamide compounds which are highly effective insecticidal and acaricidal agents useful for the control of insect and acarid pests and for protecting agronomic crops from attack by said pests.

The insecticidal and acaricidal pyrrole thiocarboxamide compounds of the present invention have the structural formula I:

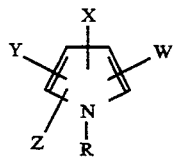

(I)

wherein
W is

$CNR_1R_2$;

$R_1$ and $R_2$ are each independently hydrogen, $C_1$–$C_4$ alkyl optionally substituted with one or more halogen atoms, or phenyl optionally substituted with one or more halogen atoms, $NO_2$ groups, CN groups, $C_1$–$C_4$ alkyl groups optionally substituted with one or more halogen atoms, or $C_1$–$C_4$ alkoxy groups optionally substituted with one or more halogen atoms;

X is Cl, Br, CN, $NO_2$, Q, $C_1$–$C_4$ alkyl substituted with one or more halogen atoms, or phenyl optionally substituted with one or more halogen atoms, $NO_2$ groups, CN groups, $C_1$–$C_4$ alkyl groups optionally substituted with one or more halogen atoms, or $C_1$–$C_4$ alkoxy groups optionally substituted with one or more halogen atoms;

Q is

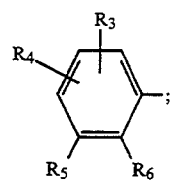

$R_3$ and $R_4$ are each independently hydrogen, halogen, $NO_2$, CN or $C_1$–$C_4$ alkyl optionally substituted with one or more halogen atoms;

$R_5$ and $R_6$ are taken together with the atoms to which they are attached to form a 5- or 6-membered heterocyclic ring containing 1 or 2 oxygen atoms and optionally substituted with one or more halogen atoms or $C_1$–$C_4$ alkyl groups optionally substituted with one or more halogen atoms;

Y is hydrogen, Cl, Br, CN, $NO_2$, $S(O)_nT$, Q, $C_1$–$C_4$ alkyl substituted with one or more halogen atoms, or phenyl optionally substituted with one or more halogen atoms, $NO_2$ groups, CN groups, $C_1$–$C_4$ alkyl groups optionally substituted with one or more halogen atoms, or $C_1$–$C_4$ alkoxy groups optionally substituted with one or more halogen atoms;

Z is hydrogen, Cl, Br, $S(O)_nT$ or $C_1$–$C_4$ alkyl substituted with one or more halogen atoms;

T is $C_1$–$C_4$ alkyl substituted with one or more halogen atoms;

n is an integer of 0, 1 or 2;

R is A, OA or CN;

A is hydrogen,

$CR_7$, $CHR_8NHCR_9$, $CH_2SQ_1$, $C_1$–$C_6$ alkyl optionally substituted with one to three halogen atoms, one tri ($C_1$–$C_4$ alkyl)silyl, one hydroxy, one cyano, one or two $C_1$–$C_4$ alkoxy groups optionally substituted with one to three halogen atoms, one $C_1$–$C_4$ alkylthio, one phenyl optionally substituted with one to three halogen atoms, one to three $C_1$–$C_4$ alkyl groups or one to three $C_1$–$C_4$ alkoxy groups, one phenoxy group optionally substituted with one to three halogen atoms, one to three $C_1$–$C_4$ alkyl groups or one to three $C_1$–$C_4$ alkoxy groups, one benzyloxy group optionally substituted on the phenyl ring with one to three halogen atoms, one to three $C_1$–$C_4$ alkyl groups or one to three $C_1$–$C_4$ alkoxy groups, one $C_1$–$C_6$ alkylcarbonyloxy group optionally substituted with one to three halogen atoms, one $C_2$–$C_6$ alkenylcarbonyloxy group optionally substituted with one to three halogen atoms, one phenylcarbonyloxy group optionally substituted with one to three halogen atoms, one to three $C_1$–$C_4$ alkyl groups or one to three $C_1$–$C_4$ alkoxy groups, one $C_1$–$C_6$ alkoxycarbonyl group optionally substituted with one to three halogen atoms or one to three $C_1$–$C_4$ alkoxy groups, or one benzylcarbonyloxy group optionally substituted on the phenyl ring with one to three halogen atoms, one to three $C_1$–$C_4$ alkyl groups or one to three $C_1$–$C_4$ alkoxy groups, $C_3$–$C_6$ alkenyl optionally substituted with one to three halogen atoms or one phenyl group, or $C_3$–$C_6$ alkynyl optionally substituted with one to three halogen atoms or one phenyl group;

$R_7$ is $C_1$–$C_6$ alkyl or $C_3$–$C_6$ cycloalkyl each optionally substituted with one to three halogen atoms, one hydroxy, one cyano, one or two $C_1$–$C_4$ alkoxy groups optionally substituted with one to three halogen atoms, one $C_1$–$C_4$ alkylthio, one phenyl group optionally substituted with one to three halogen atoms, one to three $C_1$–$C_4$ alkyl groups or one to three $C_1$–$C_4$ alkoxy groups, one phenoxy group optionally substituted with one to three halogen atoms, one to three $C_1$–$C_4$ alkyl groups or one to three $C_1$–$C_4$ alkoxy groups, one benzyloxy group optionally substituted on the phenyl ring with one to three halogen atoms, one to three $C_1$–$C_4$ alkyl groups or one to three $C_1$–$C_4$ alkoxy groups, one $C_1$–$C_6$ alkylcarbonyloxy group optionally substituted with one to three halogen atoms, one $C_2$–$C_6$ alkenylcarbonyloxy group optionally substituted with one to three halogen atoms, one phenylcarbonyloxy group optionally substituted with one to three halogen atoms, one to three $C_1$–$C_4$ alkyl groups or one to three $C_1$–$C_4$ alkoxy groups, one $C_1$–$C_6$ alkoxycarbonyl group optionally substituted with one to three halogen atoms or one to three $C_1$–$C_4$ alkoxy groups, or one benzyloxycarbonyl group optionally substituted on the phenyl ring with one to three halogen atoms, one to three $C_1$–$C_4$ alkyl groups or one to three $C_1$–$C_4$ alkoxy groups, $C_2$–$C_6$ alkenyl optionally substituted with one to three halogen atoms or one phenyl group, $C_3$–$C_6$ alkynyl optionally substituted with one to three halogen atoms or one phenyl group, phenyl optionally substituted with one or more halogen atoms, $C_1$–$C_4$ alkyl groups, $C_1$–$C_4$ alkoxy groups, phenoxy groups, $C_1$–$C_4$ alkylthio groups, tri($C_1$–$C_4$ alkyl)silyl groups, $C_1$–$C_4$ alkylsulfinyl groups, $C_1$–$C_4$ alkylsulfonyl groups, CN groups, $NO_2$ groups or $CF_3$ groups, phenoxy optionally substituted with one or more halogen atoms, $C_1$–$C_4$ alkyl groups, $C_1$–$C_4$ alkoxy groups, $C_1$–$C_4$ alkylthio groups, tri($C_1$–$C_4$alkyl)silyl groups, $C_1$–$C_4$ alkylsulfinyl groups, $C_1$–$C_4$ alkylsulfonyl groups, CN groups, $NO_2$ groups or $CF_3$ groups, 1- or 2-naphthyl, 2-, 3-, or 4-pyridyl optionally substituted with one to three halogen atoms, $C_1$–$C_6$ alkoxy optionally substituted with one to three halogen atoms, or $C_2$–$C_6$ alkenyloxy optionally substituted with one to three halogen atoms;

$R_8$ is hydrogen or $C_1$–$C_4$ alkyl;

$R_9$ is $C_1$–$C_6$ alkyl optionally substituted with one to three halogen atoms, phenyl optionally substituted with one to halogen atoms, CN groups, $NO_2$ groups, $C_1$–$C_4$ alkyl groups, $C_1$–$C_4$ alkoxy groups or $CF_3$ groups, 2- or 3-thienyl, or 2- or 3-furyl;

$Q_1$ is

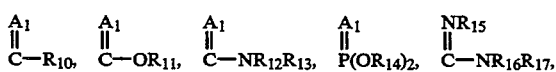

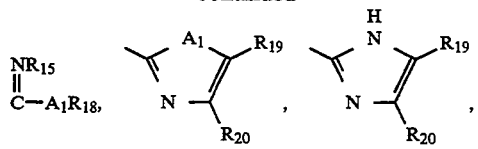

CN, $C_1$–$C_6$ alkyl optionally substituted with one or more halogen atoms, CN groups or phenyl groups, or phenyl optionally substituted with one or more halogen atoms, $C_1$–$C_4$ alkyl groups, $C_1$–$C_4$ alkoxy groups, CN groups, $NO_2$ groups, $CF_3$ groups or $NR_{21}R_{22}$ groups;

$A_1$ is O or S;

$R_{10}$ is $C_1$–$C_6$ alkyl or phenyl;

$R_{11}$ is $C_1$–$C_6$ alkyl;

$R_{12}$ and $R_{13}$ are each independently hydrogen, $C_1$–$C_6$ alkyl or may be taken together with the atom to which they are attached to form a 5- to 7-membered ring;

$R_{14}$ is $C_1$–$C_4$ alkyl;

$R_{15}$ is hydrogen, $C_1$–$C_4$ alkyl or may be taken together with either $R_{16}$ or $R_{18}$ and the atoms to which they are attached to form a 5- to 7-membered ring optionally substituted with one or two $C_1$–$C_4$ alkyl groups;

$R_{16}$ and $R_{17}$ are each independently hydrogen or $C_1$–$C_4$ alkyl;

$R_{18}$ is $C_1$–$C_4$ alkyl or when taken together with $R_{15}$ and the atoms to which they are attached may form a 5-to 7-membered ring optionally substituted with one or two $C_1$–$C_4$ alkyl groups;

$R_{19}$ and $R_{20}$ are each independently hydrogen or $C_1$–$C_4$ alkyl or when taken together may form a ring wherein $R_{19}R_{20}$ is represented by —CH=CH—CH=CH—; and $R_{21}$ and $R_{22}$ are each independently hydrogen or $C_1$–$C_4$ alkyl;

with the proviso that when W is on the 2- or 5-position of the pyrrole ring, then R is other than H.

This invention also relates to insecticidal and acaricidal compositions containing those compounds and methods for using those compounds and compositions for the control of insects and acarina and for the protection of plants from attack by insects and acarina.

DETAILED DESCRIPTION OF THE INVENTION

Insects and acarina destroy growing and harvested crops. In the United States alone, agronomic crops must compete with thousands of insect and acarid species. Accordingly, there is ongoing research to create new and more effective insecticides and acaricides for the control of insects and acarina and for the protection of plants from attack by insects and acarina.

Advantageously, the present invention provides a method for controlling insects and acarina by contacting said insects and acarina, their breeding grounds, food supply or habitat with an insecticidally or acaricidally effective amount of a formula I, pyrrole thiocarboxamide compound, provided that when W is on the 2- or 5-position of the pyrrole ring, then R is other than H.

The present invention also provides a method for protecting growing plants from attack by insects and acarina by applying to the foliage of said plants or to the soil or water in which they are growing an insecticidally or acaricidally effective amount of a formula I, pyrrole thiocarboxamide compound, provided that when W is on the 2- or 5-position of the pyrrole ring, then R is other than H.

The insecticidal and acaricidal pyrrole thiocarboxamide compounds of the present invention have the following structural formula I:

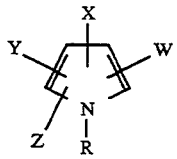

wherein
W is

$R_1$ and $R_2$ are each independently hydrogen, $C_1$–$C_4$ alkyl optionally substituted with one or more halogen atoms, or phenyl optionally substituted with one or more halogen atoms, $NO_2$ groups, CN groups, $C_1$–$C_4$ alkyl groups optionally substituted with one or more halogen atoms, or $C_1$–$C_4$ alkoxy groups optionally substituted with one or more halogen atoms;

X is Cl, Br, CN, $NO_2$, Q, $C_1$–$C_4$ alkyl substituted with one or more halogen atoms, or phenyl optionally substituted with one or more halogen atoms, $NO_2$ groups, CN groups, $C_1$–$C_4$ alkyl groups optionally substituted with one or more halogen atoms, or $C_1$–$C_4$ alkoxy groups optionally substituted with one or more halogen atoms;

Q is

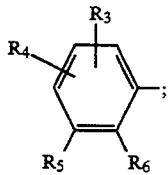

$R_3$ and $R_4$ are each independently hydrogen, halogen, $NO_2$, CN or $C_1$–$C_4$ alkyl optionally substituted with one or more halogen atoms;

$R_5$ and $R_6$ are taken together with the atoms to which they are attached to form a 5- or 6-membered heterocyclic ring containing 1 or 2 oxygen atoms and optionally substituted with one or more halogen atoms or $C_1$–$C_4$ alkyl groups optionally substituted with one or more halogen atoms;

Y is hydrogen, Cl, Br, CN, $NO_2$, $S(O)_nT$, Q, $C_1$–$C_4$ alkyl substituted with one or more halogen atoms, or phenyl optionally substituted with one or more halogen atoms, $NO_2$ groups, CN groups, $C_1$–$C_4$ alkyl groups optionally substituted with one or more halogen atoms, or $C_1$–$C_4$ alkoxy groups optionally substituted with one or more halogen atoms;

Z is hydrogen, Cl, Br, $S(O)_nT$ or $C_1$–$C_4$ alkyl substituted with one or more halogen atoms;

T is $C_1$–$C_4$ alkyl substituted with one or more halogen atoms;

n is an integer of 0, 1 or 2;

R is A, OA or CN;

A is hydrogen,

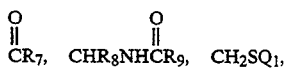

$C_1$–$C_6$ alkyl optionally substituted with one to three halogen atoms, one tri($C_1$–$C_4$ alkyl)silyl, one hydroxy, one cyano, one or two $C_1$–$C_4$ alkoxy groups optionally substituted with one to three halogen atoms, one $C_1$–$C_4$ alkylthio, one phenyl optionally substituted with one to three halogen atoms, one to three $C_1$–$C_4$ alkyl groups or one to three $C_1$–$C_4$ alkoxy groups, one phenoxy group optionally substituted with one to three halogen atoms, one to three $C_1$–$C_4$ alkyl groups or one to three $C_1$–$C_4$ alkoxy groups, one benzyloxy group optionally substituted on the phenyl ring with one to three halogen atoms, one to three $C_1$–$C_4$ alkyl groups or one to three $C_1$–$C_4$ alkoxy groups, one $C_1$–$C_6$ alkylcarbonyloxy group optionally substituted with one to three halogen atoms, one $C_2$–$C_6$ alkenylcarbonyloxy group optionally substituted with one to three halogen atoms, one phenylcarbonyloxy group optionally substituted with one to three halogen atoms, one to three $C_1$–$C_4$ alkyl groups or one to three $C_1$–$C_4$ alkoxy groups, one $C_1$–$C_6$ alkoxycarbonyl group optionally substituted with one to three halogen atoms or one to three $C_1$–$C_4$ alkoxy groups, or one benzylcarbonyloxy group optionally substituted on the phenyl ring with one to three halogen atoms, one to three $C_1$–$C_4$ alkyl groups or one to three $C_1$–$C_4$ alkoxy groups, $C_3$–$C_6$ alkenyl optionally substituted with one to three halogen atoms or one phenyl group, or $C_3$–$C_6$ alkynyl optionally substituted with one to three halogen atoms or one phenyl group;

$R_7$ is $C_1$–$C_6$ alkyl or $C_3$–$C_6$ cycloalkyl each optionally substituted with one to three halogen atoms, one hydroxy, one cyano, one or two $C_1$–$C_4$ alkoxy groups optionally substituted with one to three halogen atoms, one $C_1$–$C_4$ alkylthio, one phenyl group optionally substituted with one to three halogen atoms, one to three $C_1$–$C_4$ alkyl groups or one to three $C_1$–$C_4$ alkoxy groups, one phenoxy group optionally substituted with one to three halogen atoms, one to three $C_1$–$C_4$ alkyl groups or one to three $C_1$–$C_4$ alkoxy groups, one benzyloxy group optionally substituted on the phenyl ring with one to three halogen atoms, one to three $C_1$–$C_4$ alkyl groups or one to three $C_1$–$C_4$ alkoxy groups, one $C_1$–$C_6$ alkylcarbonyloxy group optionally substituted with one to three halogen atoms, one $C_2$–$C_6$ alkenylcarbonyloxy group optionally substituted with one to three halogen atoms, one phenylcarbonyloxy group optionally substituted with one to three halogen atoms, one to three $C_1$–$C_4$ alkyl groups or one to three $C_1$–$C_4$ alkoxy groups, one $C_1$–$C_6$ alkoxycarbonyl group optionally substituted with one to three halogen atoms or one to three $C_1$–$C_4$ alkoxy groups, or one benzyloxycarbonyl group optionally substituted on the phenyl ring with one to three halogen atoms, one to three $C_1$–$C_4$ alkyl groups or one to three $C_1$–$C_4$ alkoxy groups, $C_2$–$C_6$ alkenyl optionally substituted with one to three halogen atoms or one phenyl group, $C_3$–$C_6$ alkynyl optionally substituted with one to three halogen atoms or one phenyl group, phenyl optionally substituted with one or more halogen atoms, $C_1$–$C_4$ alkyl groups, $C_1$–$C_4$ alkoxy groups, phenoxy groups, $C_1$–$C_4$ alkylthio groups, tri($C_1$–$C_4$ alkyl)silyl groups, $C_1$–$C_4$ alkylsulfinyl groups, $C_1$–$C_4$ alkylsulfonyl groups, CN groups, $NO_2$ groups or $CF_3$ groups, phenoxy optionally substituted with one or more halogen atoms, $C_1$–$C_4$ alkyl groups, $C_1$–$C_4$ alkoxy groups, $C_1$–$C_4$ alkylthio groups, tri($C_1$–$C_4$alkyl)silyl groups, $C_1$–$C_4$ alkylsulfinyl groups, $C_1$–$C_4$ alkylsulfonyl groups, CN groups, $NO_2$ groups or $CF_3$ groups, 1- or 2-naphthyl, 2-, 3-, or 4-pyridyl optionally substituted with one to three halogen atoms, $C_1$–$C_6$ alkoxy optionally substituted with one to three halogen atoms, or $C_2$–$C_6$ alkenyloxy optionally substituted with one to three halogen atoms;

$R_8$ is hydrogen or $C_1$–$C_4$ alkyl;

$R_9$ is $C_1$–$C_6$ alkyl optionally substituted with one to three halogen atoms, phenyl optionally substituted with one to three halogen atoms, CN groups, $NO_2$ groups, $C_1$–$C_4$ alkyl groups, $C_1$–$C_4$ alkoxy groups or $CF_3$ groups, 2- or 3-thienyl, or 2- or 3-furyl;

$Q_1$ is $$\overset{A_1}{\underset{}{\overset{\|}{C}}}-R_{10}, \quad \overset{A_1}{\underset{}{\overset{\|}{C}}}-OR_{11}, \quad \overset{A_1}{\underset{}{\overset{\|}{C}}}-NR_{12}R_{13}, \quad \overset{A_1}{\underset{}{\overset{\|}{P}}}(OR_{14})_2, \quad \overset{NR_{15}}{\underset{}{\overset{\|}{C}}}-NR_{16}R_{17},$$

$$\overset{NR_{15}}{\underset{}{\overset{\|}{C}}}-A_1R_{18}, \quad \begin{array}{c} A_1 \quad R_{19} \\ \diagup \quad \diagdown \\ N \\ | \\ R_{20} \end{array}, \quad \begin{array}{c} H \\ N \quad R_{19} \\ \diagup \quad \diagdown \\ N \\ | \\ R_{20} \end{array},$$

CN, $C_1$–$C_6$ alkyl optionally substituted with one or more halogen atoms, CN groups or phenyl groups, or phenyl optionally substituted with one or more halogen atoms, $C_1$–$C_4$ alkyl groups, $C_1$–$C_4$ alkoxy groups, CN groups, $NO_2$ groups, $CF_3$ groups or $NR_{21}R_{22}$ groups;

$A_1$ is O or S;

$R_{10}$ is $C_1$–$C_6$ alkyl or phenyl;

$R_{11}$ is $C_1$–$C_6$ alkyl;

$R_{12}$ and $R_{13}$ are each independently hydrogen, $C_1$–$C_6$ alkyl or may be taken together with the atom to which they are attached to form a 5- to 7-membered ring;

$R_{14}$ is $C_1$–$C_4$ alkyl;

$R_{15}$ is hydrogen, $C_1$–$C_4$ alkyl or may be taken together with either $R_{16}$ or $R_{18}$ and the atoms to which they are attached to form a 5- to 7-membered ring optionally substituted with one or two $C_1$–$C_4$ alkyl groups;

$R_{16}$ and $R_{17}$ are each independently hydrogen or $C_1$–$C_4$ alkyl;

$R_{18}$ is $C_1$–$C_4$ alkyl or when taken together with $R_{15}$ and the atoms to which they are attached may form a 5- to 7-membered ring optionally substituted with one or two $C_1$–$C_4$ alkyl groups;

$R_{19}$ and $R_{20}$ are each independently hydrogen or $C_1$–$C_4$ alkyl or when taken together may form a ring wherein $R_{19}R_{20}$ is represented by —CH=CH—CH=CH—; and $R_{21}$ and $R_{22}$ are each independently hydrogen or $C_1$–$C_4$ alkyl;

with the proviso that when W is on the 2- or 5-position of the pyrrole ring, then R is other than H.

Preferred formula I insecticidal and acaricidal pyrrole thiocarboxamide compounds of the invention are those wherein W is $$\overset{S}{\underset{}{\overset{\|}{C}}}NR_1R_2;$$

$R_1$ and $R_2$ are each independently hydrogen or $C_1$–$C_4$ alkyl;

X is Q or phenyl optionally substituted with one or more halogen atoms, $NO_2$ groups, CN groups, $C_1$–$C_4$ alkyl groups optionally substituted with one or more halogen atoms, or $C_1$–$C_4$ alkoxy groups optionally substituted with one or more halogen atoms;

Q is

[structure: phenyl ring with O—CF$_2$—O fused below, showing dioxole with two F on the carbon]

Y is hydrogen, Cl, Br, CN, $NO_2$ or $CF_3$;

Z is hydrogen, Cl, Br or $CF_3$;

R is A or CN;

A is hydrogen, $$\overset{O}{\underset{}{\overset{\|}{C}}}R_7$$

or $C_1$–$C_6$ alkyl optionally substituted with one to three halogen atoms, one $C_1$–$C_4$ alkoxy group, one cyano, one $C_1$–$C_6$ alkylcarbonyloxy group, one benzylcarbonyloxy group, or one phenylcarbonyloxy group optionally substituted with one to three halogen atoms or one $C_1$–$C_4$ alkyl group; and $R_7$ is phenyl optionally substituted with one or more halogen atoms, $C_1$–$C_4$ alkyl groups, $C_1$–$C_4$ alkoxy groups, CN groups, $NO_2$ groups or $CF_3$ groups.

More preferred compounds of the present invention are illustrated by formula II and formula III:

[structure (II): pyrrole ring with substituents Y, W, Z, X and N—R]

wherein

W is $$\overset{S}{\underset{}{\overset{\|}{C}}}NR_1R_2;$$

$R_1$ and $R_2$ are each independently hydrogen or $C_1$–$C_4$ alkyl;

X is Q or phenyl optionally substituted with one or more halogen atoms, $NO_2$ groups, CN groups, $C_1$–$C_4$ alkyl groups optionally substituted with one or more halogen atoms, or $C_1$–$C_4$ alkoxy groups optionally substituted with one or more halogen atoms;

Q is

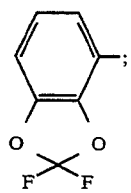

Y is hydrogen, Cl, Br or $CF_3$;
Z is Cl, Br or $CF_3$; and
R is hydrogen or $C_1$–$C_6$ alkyl substituted with one $C_1$–$C_4$ alkoxy group.

The present invention also relates to novel pyrrole thiocarboxamide compounds having the structural formula

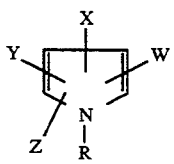

wherein W, X, Y, Z and R are as described hereinabove for formula I with the proviso that when W is on the 3-position of the pyrrole ring and X is on the 4-position of the pyrrole ring and Y, Z and R are each hydrogen, then X is other than 2- or 3-chlorophenyl; and with the proviso that when W is on the 2- or 5-position of the pyrrole ring, then R is other than H; and with the further proviso that when $R_1$ and $R_2$ are both H, then X and Y are other than phenyl optionally substituted with one or more halogen atoms, $NO_2$ groups, CN groups, $C_1$–$C_4$ alkyl groups optionally substituted with one or more halogen atoms, or $C_1$–$C_4$ alkoxy groups optionally substituted with one or more halogen atoms.

Exemplary of halogen hereinabove are fluorine, chlorine, bromine and iodine.

Certain formula I compounds of the invention wherein X is CN; Y, Z and R are hydrogen and W is as described above may be prepared as shown in Flow Diagram I.

FLOW DIAGRAM I

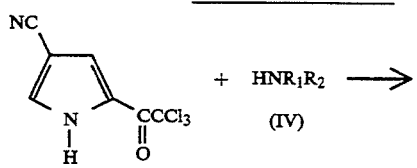

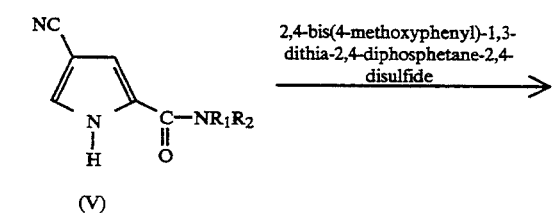

-continued
FLOW DIAGRAM I

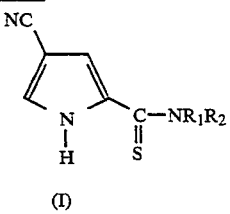

(I)

2-Trichloroacetylpyrrole-4-carbonitrile is reacted with at least about one molar equivalent of a formula IV amine compound to give a formula V 4-cyanopyrrole-2-carboxamide compound. The formula V intermediate is then reacted with at least about one molar equivalent of a reagent capable of introducing the thioxo group, such as 2,4-bis(4-methoxyphenyl)-1,3-dithia-2,4-diphosphetane-2,4-disulfide, to give the desired 4-cyanopyrrole-2-thiocarboxamide of formula I.

Other insecticidal and acaricidal compounds of formula I may be prepared as shown in Flow Diagram II.

FLOW DIAGRAM II

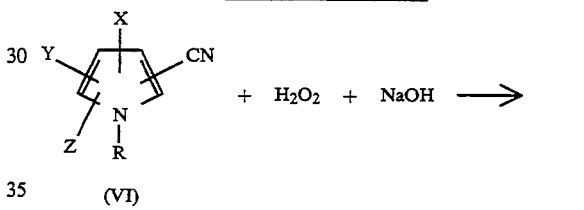

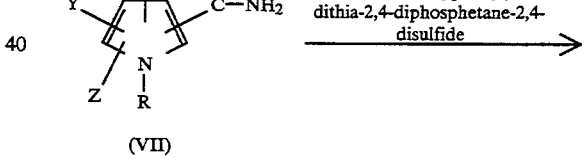

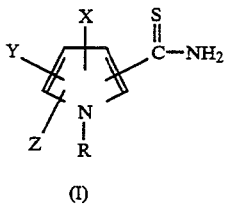

(I)

The appropriately substituted formula VI cyanopyrrole is reacted with an excess of hydrogen peroxide and sodium hydroxide to give the appropriately substituted formula VII pyrrole carboxamide. The intermediate formula VII compound is then reacted with at least about one molar equivalent of a reagent capable of introducing the thioxo group, such as 2,4-bis(4-methoxyphenyl)-1,3-dithia-2,4-diphosphetane2,4-disulfide, to give the appropriately substituted formula I pyrrole thiocarboxamide compound.

Certain inecticidal and acaricidal 4-(substituted phenyl)pyrrole-3-thiocarboxamide compounds of formula I may be prepared as shown in Flow Diagram III.

FLOW DIAGRAM III

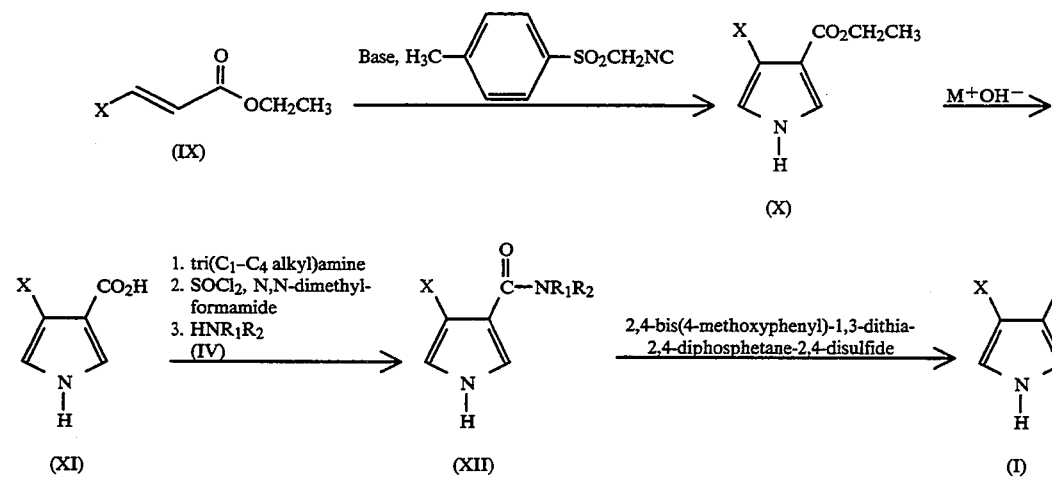

(VIII) ... (IX) ... (X) ... (XI) ... (XII) ... (I)

wherein

X is Q or phenyl optionally substituted with one or more halogen atoms, $NO_2$ groups, CN groups, $C_1-C_4$ alkyl groups optionally substituted with one or more halogen atoms, or $C_1-C_4$ alkoxy groups optionally substituted with one or more halogen atoms;

M is an alkali metal; and

Q, $R_1$ and $R_2$ are as described hereinabove for formula I.

The appropriately substituted formula VIII benzaldehyde is reacted with at least about one molar equivalent each of triethyl phosphonoacetate, lithium chloride and triethylamine to give the appropriately substituted ethyl cinnamate of formula IX. The formula IX cinnamate is reacted with at least about one molar equivalent of a strong base such as sodium hydride and at least about one molar equivalent of tosylmethyl isocyanide to give a formula X ethyl 4-(substituted phenyl)pyrrole-3-carboxylate which is hydrolyzed with an alkali metal hydroxide such as potassium hydroxide to give a formula XI 4-(substituted phenyl)pyrrole-3-carboxylic acid. The formula XI carboxylic acid is reacted with an excess of a tri($C_1-C_4$ alkyl)amine to form a first mixture. The first mixture is reacted with an excess of thionyl chloride and at least about one molar equivalent of N,N-dimethylformamide to give a second mixture. The second mixture is reacted with an excess of a formula IV amine compound to give the formula XII 4-(substituted phenyl)-pyrrole-3-carboxamide and reacting the formula XII carboxamide with a reagent capable of introducing the thioxo group, such as 2,4-bis(4-methoxyphenyl)-1,3-dithia-2,4-diphosphetane-2,4-disulfide, to give the desired insecticidal and acaricidal 4-(substituted phenyl)-pyrrole-3-thiocarboxamide of formula I.

Preparation of 1-substituted formula I pyrrole thiocarboxamide compounds can be achieved by reaction of the appropriately substituted formula I pyrrole thiocarboxamide having R as hydrogen with an alkylating or acylating agent in the presence of an alkali metal alkoxide or hydride. For example, a formula I pyrrole thiocarboxamide, wherein R is hydrogen and W, X, Y and Z are as described for formula I above, is reacted with an appropriate alkylating agent such as a $C_1-C_6$ alkylhalide in which the alkyl group is straight or branched and is optionally substituted with from one to three halogen atoms, one hydroxy, one cyano, one $C_1-C_4$ alkoxy, one $C_1-C_4$ alkylthio, one phenyl group optionally substituted with from one to three halogen atoms, or one benzyloxy group optionally substituted with from one to three halogen atoms, and an alkali metal alkoxide such as sodium or potassium t-butoxide. This reaction provides a pyrrole thiocarboxamide having the same substituents as the starting material, but in addition is substituted on the nitrogen with a $C_1-C_6$ alkyl group optionally substituted as described above. This reaction may be illustrated as follows:

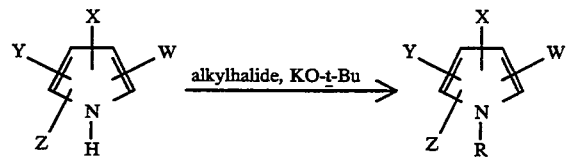

wherein W, X, Y and Z are as described for formula I above and R is $C_1-C_6$ alkyl optionally substituted as described above. In a similar reaction cyanogen bromide is substituted for the alkylhalide and yields the formula I pyrrole thiocarboxamide having a carbonitrile, rather than an alkyl group on the 1-position.

Advantageously, the above-described alkylation procedure of the formula I pyrrole thiocarboxamide compounds in which R is hydrogen may also be applied to the preparation of formula I pyrrole thiocarboxamides having an N-$C_3-C_6$ alkenyl or N-$C_3-C_6$ alkynyl substituent. This substitution is obtained by simply substituting a $C_3-C_6$ alkenyl halide or $C_3-C_6$ alkynyl halide for the $C_1-C_6$ alkyl halide in the above-described reaction.

In a similar manner, preparation of 1-acylated pyrrole thiocarboxamides may be achieved by the reaction of an appropriately substituted formula I pyrrole thiocarboxamide wherein R is hydrogen with an acylating agent in the presence of an alkali metal alkoxide. Acylating agents such as $C_1-C_6$ alkyl or $C_2-C_6$ alkenyl acid chlorides, substituted $C_1-C_6$ alkyl or $C_2-C_6$ alkenyl acid chlorides, benzoyl chloride, substituted benzoyl chlorides, phenylchloroformate, substituted phenylchloroformates, $C_1-C_6$ alkyl or $C_2-C_6$ alkenylchloroformates, substituted $C_1-C_6$ alkyl or $C_2-C_6$ alkenylchloroformates, N-substituted carbamoyl chlorides and the like may be employed. The reaction may be illustrated as follows:

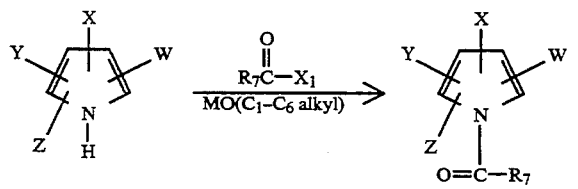

wherein $X_1$ is halogen, M is an alkali metal and W, X, Y, Z and $R_7$ are as described hereinabove for formula I.

Formula I pyrrole thiocarboxamide compounds wherein R is $CH_2SQ_1$ may be prepared by reaction of the appropriately substituted formula I pyrrole thiocarboxamide having A as chloromethyl with an alkali metal salt of an $SQ_1$ compound in the presence of a base. And formula I pyrrole thiocarboxamide compounds wherein R is $CHR_8NHC(O)R_9$ may be prepared as shown below.

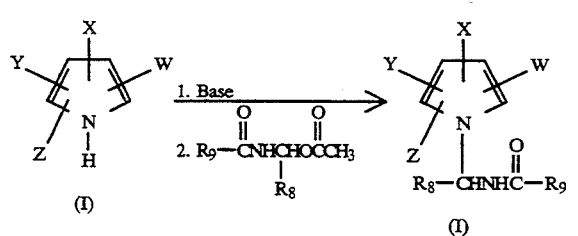

Advantageously, 1-halomethyl pyrrole thiocarboxamides of formula I may be prepared as shown below.

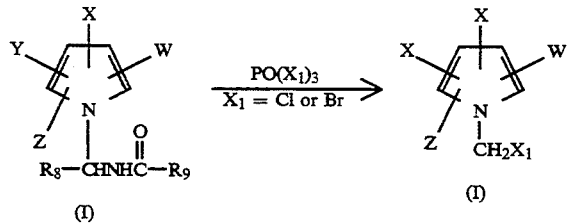

Other methods for the preparation of formula I pyrrole thiocarboxamides will become apparent from the examples set forth below.

The pyrrole thiocarboxamide compounds of the present invention are effective for controlling insects and acarina. Those compounds are also effective for protecting growing or harvested crops from attack by insects and acarina.

In practice generally about 10 ppm to 10,000 ppm and preferably 100 ppm to about 5,000 ppm of a formula I pyrrole thiocarboxamide compound, dispersed in water, or another liquid carrier, is effective when applied to the plants, the crops or the soil in which said crops are growing to protect said crops from attack by insects and acarina.

The formula I compounds of this invention are also effective for controlling insects and acarina, when applied to the foliage of plants and/or to the soil or water in which said plants are growing in sufficient amount to provide a rate of from about 0.100 kg/ha to 4.0 kg/ha of active ingredient.

While the compounds of this invention are effective for controlling insects and acarina when employed alone, they may also be used in combination with insecticidally and acaricidally effective amounts of one or more other biological chemicals. For example, the formula I compounds of this invention may be used effectively in conjunction or combination with phosphates, carbamates, cyclodienes, endotoxin of bacillus thuringiensis (Bt), phenol tin compounds, pyrethroids, formamidines, chlorinated hydrocarbons, benzoylphenyl ureas and the like.

The compounds of the invention may be formulated as emulsifiable concentrates, flowable concentrates, or wettable powders which are diluted with water or other suitable polar solvent, generally in situ, and then applied as a dilute spray. Said compounds may also be formulated in dry compacted granules, granular formulations, dusts, dust concentrates, suspension concentrates, microemulsions and the like all of which lend themselves to seed, soil, water and/or foliage applications to provide the requisite plant protection. Such formulations include the compounds of the invention admixed with inert, solid or liquid diluents.

For example, wettable powders, dusts, and dust concentrate formulations can be prepared by grinding and blending together about 25% to about 85% by weight of formula I compounds and about 75% to about 15% by weight of a solid diluent such as bentonite, diatomaceous earth, kaolin, attapulgite, or the like, about 1% to about 5% by weight of a dispersing agent such as sodium lignosulfonate, and about 1% to 5% by weight of a nonionic surfactant, such as octylphenoxy polyethoxy ethanol, nonylphenoxy polyethoxy ethanol or the like.

A typical emulsifiable concentrate can be prepared by dissolving about 15% to about 70% by weight of a pyrrole thiocarboxamide compound in about 85% to about 30% by weight of a solvent such as isophorone, toluene, butyl cellosolve, methyl acetate, propylene glycol monomethyl ether, or the like and dispersing therein about 1% to 5% by weight of a nonionic surfactant such as an alkylphenoxy polyethoxy alcohol.

In order to facilitate a further understanding of the invention, the following examples are presented primarily for the purpose of illustrating more specific details thereof. The examples generally utilize the above reaction schemes and also provide further means for preparing even more compounds of the present invention which are not specifically described above. The invention should not be deemed limited by the examples as the full scope of the invention is defined in the claims.

EXAMPLE 1

Preparation of 4-Cyanopyrrole-2-carboxamide

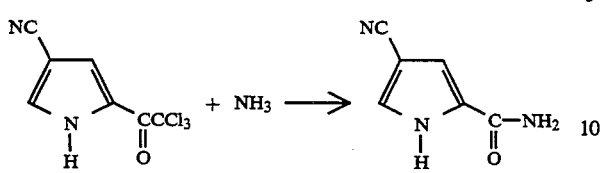

A solution of 2-trichloroacetylpyrrole-4-carbonitrile (20 g, 84.2 mmol) in methanol is treated with ammonia (51 mL), stirred at room temperature for 30 minutes and diluted with water. The aqueous mixture is filtered to obtain the title product as a white solid (7.0 g, mp 253°–256° C.).

EXAMPLE 2

Preparation of 4-Cyanopyrrole-2-thiocarboxamide

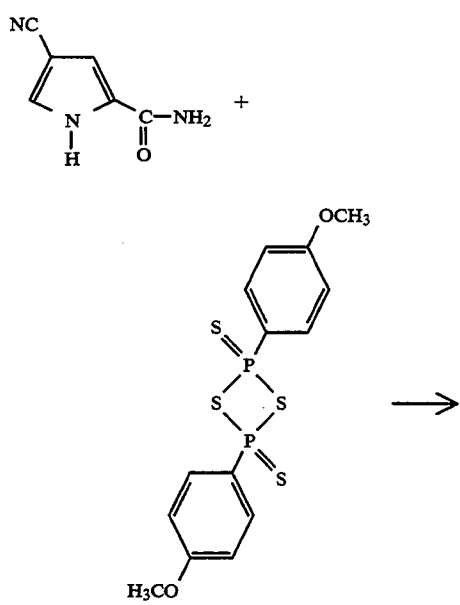

A mixture of 4-cyanopyrrole-2-carboxamide (1.35 g, 10.0 mmol) and 2,4-bis(4-methoxyphenyl)-1,3-dithia-2,4-diphosphetane-2,4-disulfide (4.0 g, 9.9 mmol) in toluene is heated at 100° C. for 4½ hours, diluted with tetrahydrofuran and heated at reflux for 20 minutes. The reaction mixture is then cooled and concentrated in vacuo to obtain a residue. Chromatography of the residue using silica gel and a 4:1 hexanes/ethyl acetate mixture gives the title product as a yellow solid (0.9 g, mp 253° C. dec.).

EXAMPLE 3

Preparation of 4-Bromo-2-(p-chlorophenyl)-1-(ethoxymethyl)-5-(trifluoromethyl)pyrrole-3-carboxamide

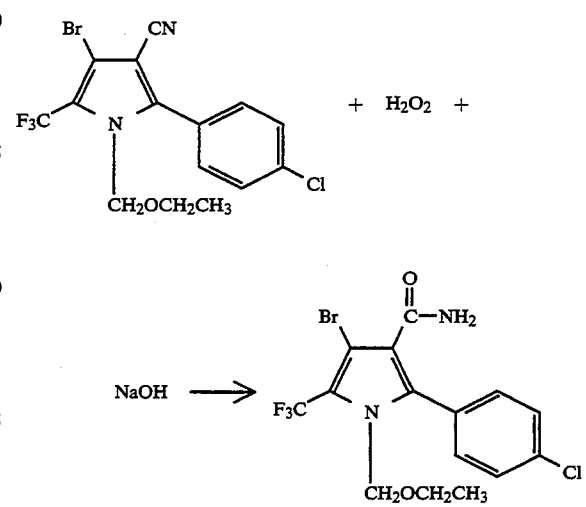

A mixture of 4-bromo-2-(p-chlorophenyl)-1-(ethoxymethyl)-5-(trifluoromethyl)pyrrole-3-carbonitrile (4.07 g, 10 mmol), sodium hydroxide (0.8 g, 20 mmol) and 30 wt/wt % hydrogen peroxide solution (7.2 mL, 70 mmol) in methanol is stirred at room temperature for 7 hours, treated with sodium hydroxide solution (0.8 g NaOH in 5 mL of H$_2$O) and 30 wt/wt % hydrogen peroxide solution (7 mL), stirred at room temperature overnight, heated at 40° C. for 8 hours and diluted with water. The aqueous mixture is filtered and the filter cake is washed with water and heptane and dried to give the title product as a white solid (3.7 g) which is identified by $^1$H and $^{13}$C NMR spectral analyses.

EXAMPLE 4

Preparation of 4-Bromo-2-(p-chlorophenyl)-1-ethoxymethyl)-5-(trifluoromethyl)pyrrole-3-thiocarboxamide

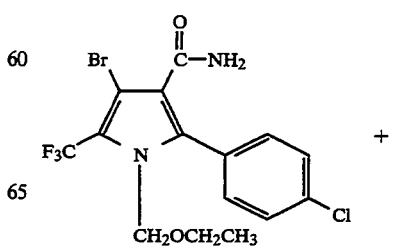

-continued

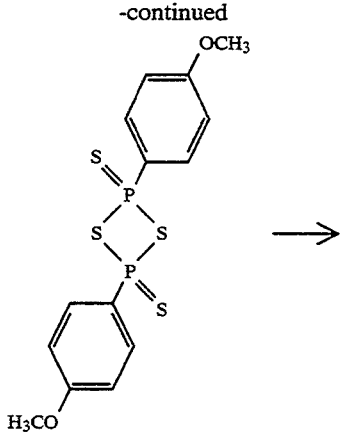

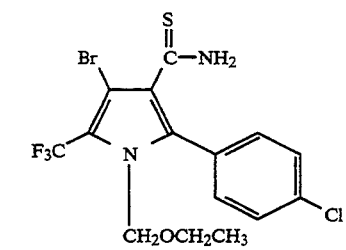

A mixture of 4-bromo-2-(p-chlorophenyl)-1-(ethoxymethyl)-5-(trifluoromethyl)pyrrole-3-carboxamide (3.9 g, 9.2 mmol) and 2,4-bis(4-methoxyphenyl)-1,3-dithia-2,4-diphosphetane-2,4-disulfide (5.7 g, 14.1 mmol) in acetonitrile is heated at reflux for 6 hours, cooled and concentrated in vacuo to obtain a residue. Chromatography of the residue using silica gel and a 4:1 hexanes/ethyl acetate mixture gives the title product as a yellow solid (1.5 g, mp 163°–172° C.).

EXAMPLE 5

Preparation of 2,4,5-Tribromo-1-methylpyrrole-3-thiocarboxamide

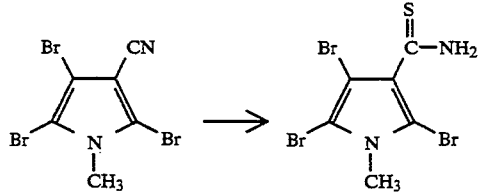

Diisopropylethylamine (1.1 mL, 6 mmol), 2,4,5-tribromo-1-methylpyrrole-3-carbonitrile (2.16 g, 6 mmol) and pyridine (10 mL) are added to condensed hydrogen sulfide in a pressure tube at −78° C. The tube is sealed and the reaction mixture is stirred for 5 days at room temperature. The reaction mixture is then concentrated in vacuo to obtain a residue. Chromatography of the residue using silica gel and a 4:1 hexanes/ethyl acetate mixture gives the title product as a yellow solid (0.47 g, mp 100.5°–102° C. dec.).

EXAMPLE 6

Preparation of Ethyl 2,3-dichlorocinnamate, (E)-

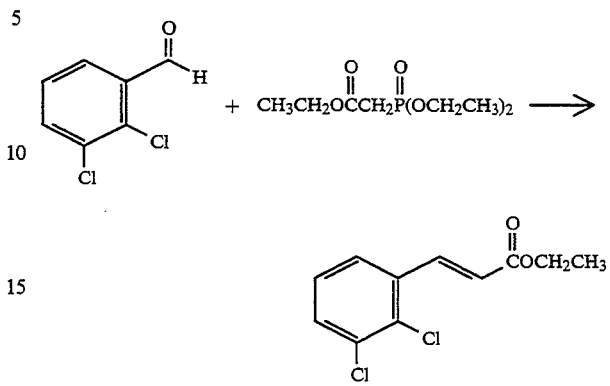

A mixture of 2,3-dichlorobenzaldehyde (17.5 g, 0.1 mol), triethyl phosphonoacetate (22.4 g, 0.12 mol), lithium chloride (5.1 g, 0.12 mol) and triethylamine (17 mL, 0.12 mol) in acetonitrile is stirred at room temperature for 1 hour and diluted with a water/ethyl acetate mixture. The organic phase is separated, washed with water dried over anhydrous Na$_2$SO$_4$ and concentrated in vacuo to give the title product as a yellow solid (42 g).

EXAMPLE 7

Preparation of Ethyl 4-(2,3-dichlorophenyl)pyrrole-3-carboxylate

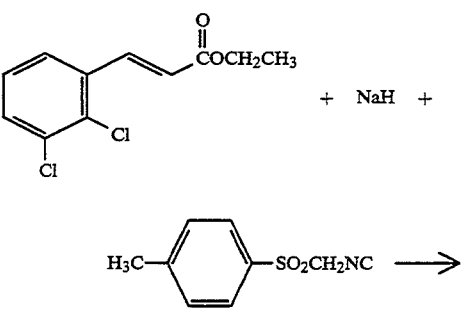

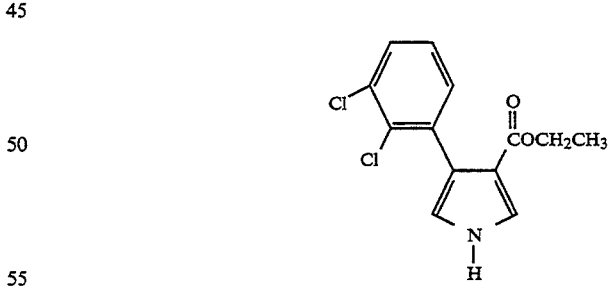

Sodium hydride (3.2 g, 60% in mineral oil) is washed with petroleum ether and suspended in tetrahydrofuran. A mixture of ethyl 2,3-dichlorocinnamate, (E)- (12.25 g, 50 mmol) and tosylmethyl isocyanide (11.7 g, 60 mmol) in tetrahydrofuran is added to the sodium hydride/tetrahydrofuran mixture. The reaction mixture is stirred for 1 hour, quenched with saturated ammonium chloride solution and extracted with diethyl ether. The organic extracts are combined, washed with water, dried over anhydrous Na$_2$SO$_4$ and concentrated in vacuo to obtain a residue. Chromatography of the residue using silica gel and a 2:1 hexanes/ethyl acetate mixture gives

EXAMPLE 8

Preparation of
4-(2,3-Dichlorophenyl)pyrrole-3-carboxylic acid

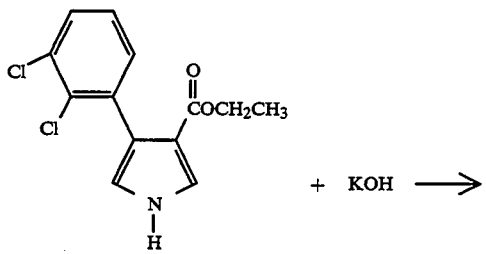

+ KOH →

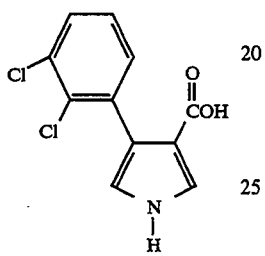

A mixture of ethyl 4-(2,3-dichlorophenyl)pyrrole-3-carboxylate (5.95 g, 21 mmol) and potassium hydroxide (6.5 g, 85%, 99 mmol) is heated at reflux for 6 hours, cooled, diluted with water and washed with diethyl ether. The aqueous phase is acidified with hydrochloric acid and filtered to obtain a solid. The solid is washed with diethyl ether and petroleum ether and dried to give the title product as a white solid (5.24 g) which is identified by $^1$H and $^{13}$C NMR spectral analyses.

EXAMPLE 9

Preparation of
4-(2,3-Dichlorophenyl)pyrrole-3-carboxamide

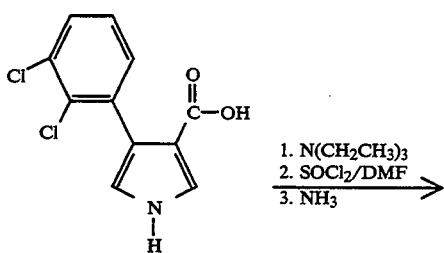

1. N(CH$_2$CH$_3$)$_3$
2. SOCl$_2$/DMF
3. NH$_3$
→

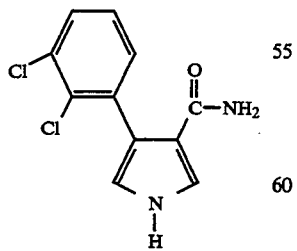

A mixture of 4-(2,3-dichlorophenyl)pyrrole-3-carboxylic acid (2.43 g, 9.5 mmol) and triethylamine (7 mL, 50 mmol) in tetrahydrofuran is stirred for 15 minutes at room temperature and concentrated in vacuo to obtain a residue. A mixture of the residue, thionyl chloride (2.77 mL, 38 mmol) and N,N-dimethylformamide (0.73 mL, 9.5 mmol) is stirred overnight at room temperature and concentrated in vacuo to obtain a yellow oil. The oil is added to a concentrated ammonia solution and stirred for 1 hour. This mixture is filtered to give a solid. The solid is washed with water, dried and chromatographed using silica gel and a 4:1 hexanes/ethyl acetate mixture to obtain the title product as a white solid (1.6 g, mp 185°–190° C.).

Using essentially the same procedure, but substituting the appropriate amine for ammonia, the following compounds are obtained:

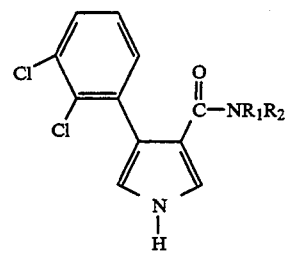

| R$_1$ | R$_2$ | mp °C. |
|---|---|---|
| H | CH$_3$ | 134–137 |
| CH$_3$ | CH$_3$ | 133–136 |

EXAMPLE 10

Preparation of
4-(2,3-Dichlorophenyl)pyrrole-3-thiocarboxamide

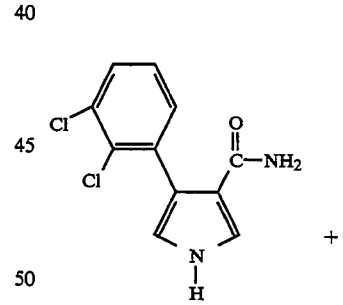

+

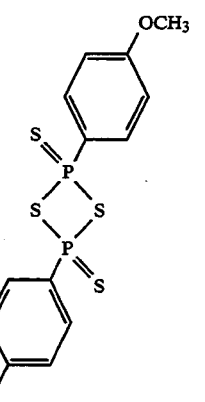

→

-continued

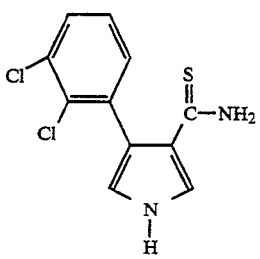

A mixture of 4-(2,3-dichlorophenyl)pyrrole-3-carboxamide (0.98 g, 3.8 mmol) and 2,4-bis(4-methoxyphenyl)-1,3-dithia-2,4-diphosphetane-2,4-disulfide (0.77 g, 1.9 mmol) in tetrahydrofuran is heated at reflux for 75 minutes, cooled and concentrated in vacuo to obtain a residue. Chromatography of the residue using silica gel and a 1:1 hexane/ethyl acetate mixture gives the title product as a yellow solid (0.54 g, mp 128°-132° C.).

Using essentially the same procedure, but using the appropriately substituted pyrrole carboxylic amide, the following compounds are obtained:

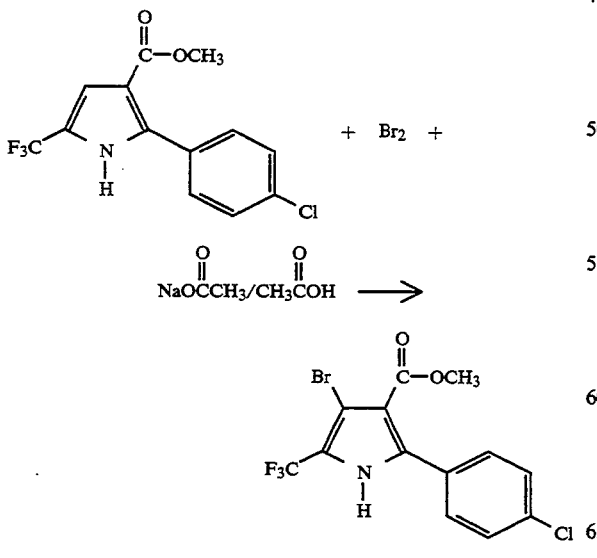

| $R_1$ | $R_2$ | mp °C. |
|---|---|---|
| H | $CH_3$ | 158–162 |
| $CH_3$ | $CH_3$ | 226–229 |

EXAMPLE 11

Preparation of Methyl 4-bromo-2-(p-chlorophenyl)-5-(trifluoromethyl)pyrrole-3-carboxylate

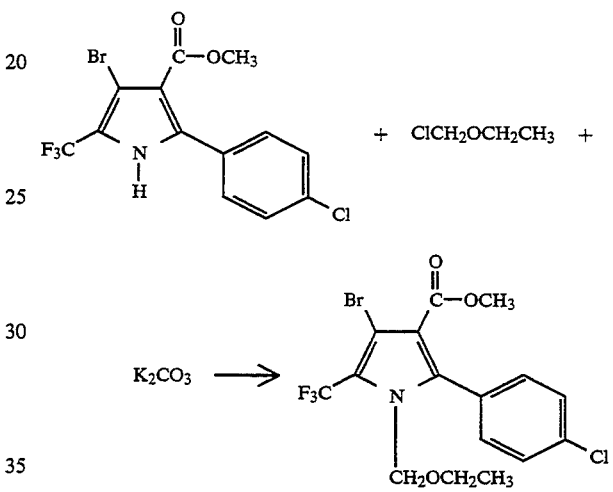

Bromine (2.3 mL, 43.7 mmol) is added to a solution of methyl 2-(p-chlorophenyl)-5-(trifluoromethyl)pyrrole-3-carboxylate (8.44 g, 29.2 mmol) and sodium acetate (3.6 g, 43.7 mmol) in acetic acid. The reaction mixture is stirred for 30 minutes, diluted with a 0.4 wt/wt% sodium sulfite solution and extracted with diethyl ether. The organic extracts are combined, washed with saturated sodium hydrogen carbonate solution, dried over anhydrous $Na_2SO_4$ and concentrated in vacuo to obtain an oil which solidifies to give the title product as a solid (9.2 g) which is identified by $^1H$ and $^{13}C$ NMR spectral analyses.

EXAMPLE 12

Preparation of Methyl 4-bromo-2-(p-chlorophenyl)-1-(ethoxymethyl)-5-(trifluoromethyl)pyrrole-3-carboxylate

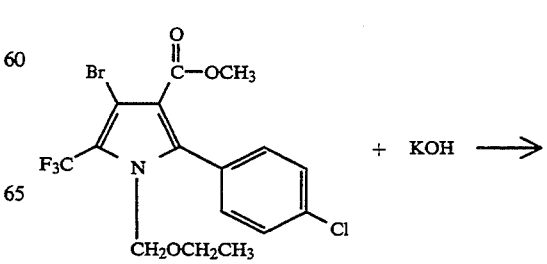

A mixture of methyl 4-bromo-2-(p-chlorophenyl)-5-(trifluoromethyl)pyrrole-3-carboxylate (9.2 g, 24.1 mmol), potassium carbonate (4.96 g, 36 mmol) and chloromethyl ethyl ether (3.3 mL, 36 mmol) is stirred at room temperature for 21 hours, treated with potassium carbonate (4.9 g) and chloromethyl ethyl ether (3.3 mL), stirred for 1 hour, treated with potassium carbonate (4.9 g) and chloromethyl ethyl ether (3.3 mL) stirred for 3 hours, diluted with water and extracted with diethyl ether. The combined organic extracts are washed with water, dried over anhydrous $MgSO_4$ and concentrated in vacuo to obtain the title product as a brown oil (13.1 g) which is used in the next step without further purification.

EXAMPLE 13

Preparation of 4-Bromo-2-(p-chlorophenyl)-1-(ethoxymethyl)-5-(trifluoromethyl)pyrrole-3-carboxylic acid

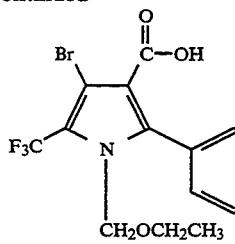

A mixture of methyl 4-bromo-2-(p-chlorophenyl)-1-(ethoxymethyl)-5-(trifluoromethyl)pyrrole-3-carboxylate (13.1 g) and potassium hydroxide (3.12 g, 85%, 48 mmol) is stirred at room temperature for 20 hours, stirred at reflux for 2 hours, diluted with water, washed with diethyl ether, acidified to pH 4 with 1N hydrochloric acid and filtered to obtain a solid. The solid is washed with water and petroleum ether and dried to give the title product as a white solid (6.45 g) which is identified by $^1$H NMR spectral analysis.

EXAMPLE 14

Preparation of 4-Bromo-2-(p-chlorophenyl)-1-(ethoxymethyl)-N-methyl-5-(trifluoromethyl)pyrrole-3-thiocarboxamide

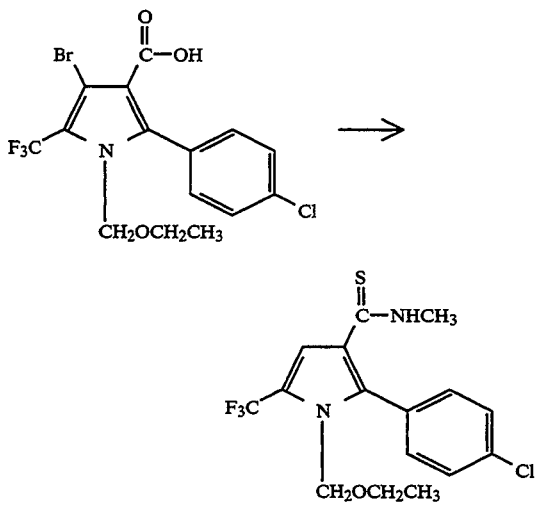

Isobutylchloroformate (0.3 mL, 2.3 mmol) is added to a mixture of 4-bromo-2-(p-chlorophenyl)-1-(ethoxymethyl)-5-(trifluoromethyl)pyrrole-3-carboxylic acid (0.83 g, 2 mmol) and triethylamine (0.33 mL, 2.3 mmol) in tetrahydrofuran at 0° C. The mixture is stirred for 1 hour at 0° C., treated with a 6 wt/wt % methylamine solution (10.6 g, 20 mmol), stirred at room temperature for 2 hours and diluted with a diethyl ether/water mixture. The organic phase is separated, dried over anhydrous $Na_2SO_4$, concentrated in vacuo, diluted with toluene and concentrated in vacuo to obtain a liquid. A mixture of the liquid in tetrahydrofuran is treated with 2,4-bis(4-methoxyphenyl)-1,3-dithia-2,4-diphosphetane-2,4-disulfide (0.40 g, 1 mmol), heated at reflux for 2 hours, concentrated in vacuo and chromatographed on silica gel with a 4:1 hexane/ethyl acetate mixture to obtain the title product as a yellow gum (0.3 g) which is identified by $^1$H and $^{13}$C NMR spectral analyses.

Using essentially the same procedure, but substituting dimethylamine for methylamine, 4-bromo-2-(p-chlorophenyl)-1-(ethoxymethyl)-N,N-dimethyl-5-(trifluoromethyl)pyrrole-3-thiocarboxamide is obtained as a yellow gum.

EXAMPLE 15

Insecticide and acaricide evaluations

The following tests show the efficacy of the compounds as insecticides and acarides. The evaluations are conducted with solutions of test compounds dissolved or dispersed in 50/50 acetone/water mixtures. The test compound is technical material dissolved or dispersed in said acetone/water mixtures in sufficient amount to provide the concentrations set forth in Table I below.

All concentrations reported herein are in terms of active ingredient. All tests are conducted in a laboratory maintained at about 27° C. The rating system employed is as follows:

| Rating System | |
|---|---|
| 0 = no effect | 5 = 56–65% kill |
| 1 = 10–25% kill | 6 = 66–75% kill |
| 2 = 26–35% kill | 7 = 76–85% kill |
| 3 = 36–45% kill | 8 = 86–99% kill |
| 4 = 46–55% kill | 9 = 100% kill |
| | — = not evaluated |

The test species of insects used in the present evaluations along with specific test procedures are described below.

*Spodoptera eridania* 3rd instar larvae, southern armyworm

A sieva lima bean leaf expanded to 7 to 8 cm in length is dipped in the test suspension with agitation for 3 seconds and placed in a hood to dry. The leaf is then placed in a 100×10 mm petri dish containing a damp filter paper on the bottom and 10 3rd instar caterpillars. The dish is maintained for 5 days before observations are made of mortality, reduced feeding, or any interference with normal moulting.

*Tetranychus urticae* (OP-resistant strain), 2-spotted spider mite

Sieva lima bean plants with primary leaves expanded to 7 to 8 cm are selected and cut back to one plant per pot. A small piece is cut from a leaf taken from the main colony and placed on each leaf of the test plants. This is done about 2 hours before treatment to allow the mites to move over to the test plant and to lay eggs. The size of the cut piece is varied to obtain about 100 mites per leaf. At the time of the treatment, the piece of leaf used to transfer the mites is reoved and discarded. The mite-infested plants are dipped in the test formulation for 3 seconds with agitation and set in the hood to dry. Plants are kept for 2 days before estimates of adult kill are made.

*Heliothis virenscens*, 3rd instar tobacco budworm

Cotton cotyledons are dipped in the test formulation and allowed to dry in a hood. When dry, each is cut into quarters and ten sections placed individually in 30 mL plastic medicine cups containing a 5 to 7 mm long piece of damp dental wick. One 3rd instar caterpillar is added to each cup and a cardboard lid is placed on the cup. Treatments are maintained for 3 days before mortality counts and estimates of reduction in feeding damage are made.

*Dibrotic undecimpunctata howardi*, 3rd instar southern corn rootworm

One cc of fine talc is placed in a 30 mL wide-moputh screw-top glass jar. One mL of the appropriate acetone test solution is pipetted onto the talc so as to provide 1.25 mg and 0.25 mg of active ingredient per jar. The jars are set under a gentle air flow until the acetone is evaporated. The dried talc is loosened, 1 cc of millet seed is added to serve as food for the insects and 25 mL of moist soil is added to each jar. The jars are capped and contents thoroughly mixed on a Vortex Mixer. Following this, ten 3rd instar rootworms are added to each jar and the jars are loosely capped to allow air exchange for the larvae. The treatments are held for 6 days before mortality counts are made. Missing larvae are presumed dead, since they decompose rapidly and can not be found. The concentrations used in this test correspond approximately to 50 kg/ha and 10 kg/ha, respectively.

The data obtained for the above described evaluations are reported in Table I.

TABLE I

| | Insecticide and Acaricide Evaluations | | | | | | | |
|---|---|---|---|---|---|---|---|---|
| | Armyworm (ppm) | | | OP. Resistant Mites (ppm) | | Tobacco Budworm (ppm) | Southern Corn Rootworm (kg/ha) | |
| Compound | 1000 | 100 | 10 | 300 | 100 | 100 | 50 | 10 |
| 4-Cyanopyrrole-2-thiocarboxamide | 9 | — | — | 0 | — | — | 9 | — |
| 4-Bromo-2-(p-chlorophonyl)-1-(ethoxymethyl)-5-(trifluoromethyl)pyrrole-3-thiocarboxamide | 9 | 9 | 9 | 9 | 9 | 9 | 9 | 9 |
| 4-Bromo-2-(p-chlorophonyl)-1-(ethoxymethyl)-N-Methyl-5-(trifluoromethyl)pyrrole-3-thiocarboxamide | — | 9 | — | 3 | — | — | — | — |
| 4-Bromo-2-(p-chlorophenyl)-1-(ethoxymethyl)-N,N-dimethyl-5-(trifluoromethyl)pyrrole-3-thiocarboxamide | — | — | — | 5 | 5 | — | — | — |

We claim:

1. A method for controlling insects and acarina which comprises contacting said insects and acarina, their breeding grounds, food supply or habitat with an insecticidally or acaricidally effective amount of a compound having the structural formula

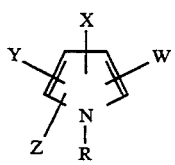

wherein
W is

$R_1$ and $R_2$ are each independently hydrogen,
  $C_1$–$C_4$ alkyl optionally substituted with one or more halogen atoms, or
  phenyl optionally substituted with one or more halogen atoms, $NO_2$ groups, CN groups, $C_1$–$C_4$ alkyl groups optionally substituted with one or more halogen atoms, or $C_1$–$C_4$ alkoxy groups optionally substituted with one or more halogen atoms;

x is Cl, Br, CN, $NO_2$, Q,
  $C_1$–$C_4$ alkyl substituted with one or more halogen atoms, or
  phenyl optionally substituted with one or more halogens atoms, $NO_2$ groups, CN groups, $C_1$–$C_4$ alkyl groups optionally substituted with one or more halogen atoms, or $C_1$–$C_4$ alkoxy groups optionally substituted with one or more halogen atoms;

Q is

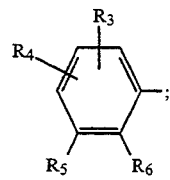

$R_3$ and $R_4$ are each independently hydrogen, halogen, $NO_2$, CN or $C_1$–$C_4$ alkyl optionally substituted with one or more halogen atoms;

$R_5$ and $R_6$ are taken together with the atoms to which they are attached to form a 5- or 6-membered heterocyclic ring containing 1 or 2 oxygen atoms and optionally substituted with one or more halogen atoms or $C_1$–$C_4$ alkyl groups optionally substituted with one or more halogen atoms;

Y is hydrogen, Cl, Br, CN, $NO_2$, $S(O)_nT$, Q,
  $C_1$–$C_4$ alkyl substituted with one or more halogen atoms, or
  phenyl optionally substituted with one or more halogen atoms, $NO_2$ groups, CN groups, $C_1$–$C_4$ alkyl groups optionally substituted with one or more halogen atoms, or $C_1$–$C_4$ alkoxy groups optionally substituted with one or more halogen atoms;

Z is hydrogen, Cl, Br, $S(O)_nT$ or $C_1$–$C_4$ alkyl substituted with one or more halogen atoms;

T is $C_1$–$C_4$ alkyl substituted with one or more halogen atoms;

n is an integer of 0, 1 or 2;

R is A, OA or CN;

A is hydrogen,

C$_1$–C$_6$ alkyl optionally substituted with one to three halogen atoms, one tri(C$_1$–C$_4$ alkyl)silyl, one hydroxy, one cyano, one or two C$_1$–C$_4$ alkoxy groups optionally substituted with one to three halogen atoms, one C$_1$–C$_4$ alkylthio, one phenyl optionally substituted with one to three halogen atoms, one to three C$_1$–C$_4$ alkyl groups or one to three C$_1$–C$_4$ alkoxy groups, one phenoxy group optionally substituted with one to three halogen atoms, one to three C$_1$–C$_4$ alkyl groups or one to three C$_1$–C$_4$ alkoxy groups, one benzyloxy group optionally substituted on the phenyl ring with one to three halogen atoms, one to three C$_1$–C$_4$ alkyl groups or one to three C$_1$–C$_4$ alkoxy groups, one C$_1$–C$_6$ alkylcarbonyloxy group optionally substituted with one to three halogen atoms, one C$_2$–C$_6$ alkenylcarbonyloxy group optionally substituted with one to three halogen atoms, one phenylcarbonyloxy group optionally substituted with one to three halogen atoms, one to three C$_1$–C$_4$ alkyl groups or one to three C$_1$–C$_4$ alkoxy groups, one C$_1$–C$_6$ alkoxycarbonyl group optionally substituted with one to three halogen atoms or one to three C$_1$–C$_4$ alkoxy groups, or one benzylcarbonyloxy group optionally substituted on the phenyl ring with one to three halogen atoms, one to three C$_1$–C$_4$ alkyl groups or one to three C$_1$–C$_4$ alkoxy groups, C$_3$–C$_6$ alkenyl optionally substituted with one to three halogen atoms or one phenyl group, or C$_3$–C$_6$ alkynyl optionally substituted with one to three halogen atoms or one phenyl group;

R$_7$ is C$_1$–C$_6$ alkyl or C$_3$–C$_6$ cycloalkyl each optionally substituted with one to three halogen atoms, one hydroxy, one cyano, one or two C$_1$–C$_4$ alkoxy groups optionally substituted with one to three halogen atoms, one C$_1$–C$_4$ alkylthio, one phenyl group optionally substituted with one to three halogen atoms, one to three C$_1$–C$_4$ alkyl groups or one to three C$_1$–C$_4$ alkoxy groups, one phenoxy group optionally substituted with one to three halogen atoms, one to three C$_1$–C$_4$ alkyl groups or one to three C$_1$–C$_4$ alkoxy groups, one benzyloxy group optionally substituted on the phenyl ring with one to three halogen atoms, one to three C$_1$–C$_4$ alkyl groups or one to three C$_1$–C$_4$ alkoxy groups, one C$_1$–C$_6$ alkylcarbonyloxy group optionally substituted with one to three halogen atoms, one C$_2$–C$_6$ alkenylcarbonyloxy group optionally substituted with one to three halogen atoms, one phenylcarbonyloxy group optionally substituted with one to three halogen atoms, one to three C$_1$–C$_4$ alkyl groups or one to three C$_1$–C$_4$ alkoxy groups, one C$_1$–C$_6$ alkoxycarbonyl group optionally substituted with one to three halogen atoms or one to three C$_1$–C$_4$ alkoxy groups, or one benzyloxycarbonyl group optionally substituted on the phenyl ring with one to three halogen atoms, one to three C$_1$–C$_4$ alkyl groups or one to three C$_1$–C$_4$ alkoxy groups, C$_2$–C$_6$ alkenyl optionally substituted with one to three halogen atoms or one phenyl group, C$_3$–C$_6$ alkynyl optionally substituted with one to three halogen atoms or one phenyl group, phenyl optionally substituted with one or more halogen atoms, C$_1$–C$_4$ alkyl groups, C$_1$–C$_4$ alkoxy groups, phenoxy groups, C$_1$–C$_4$ alkylthio groups, tri(C$_1$–C$_4$ alkyl)silyl groups, C$_1$–C$_4$ alkylsulfinyl groups, C$_1$–C$_4$ alkylsulfonyl groups, CN groups, NO$_2$ groups or CF$_3$ groups, phenoxy optionally substituted with one or more halogen atoms, C$_1$–C$_4$ alkyl groups, C$_1$–C$_4$ alkoxy groups, C$_1$–C$_4$ alkylthio groups, tri(C$_1$–C$_4$ alkyl)silyl groups, C$_1$–C$_4$ alkylsulfinyl groups, C$_1$–C$_4$ alkylsulfonyl groups, CN groups, NO$_2$ groups or CF$_3$ groups, 1- or 2-naphthyl, 2-, 3-, or 4-pyridyl optionally substituted with one to three halogen atoms, C$_1$–C$_6$ alkoxy optionally substituted with one to three halogen atoms, or C$_2$–C$_6$ alkenyloxy optionally substituted with one to three halogen atoms;

R$_8$ is hydrogen or C$_1$–C$_4$ alkyl;

R$_9$ is C$_1$–C$_6$ alkyl optionally substituted with one to three halogen atoms, phenyl optionally substituted with one to three halogen atoms, CN groups, NO$_2$ groups, C$_1$–C$_4$ alkyl groups, C$_1$–C$_4$ alkoxy groups or CF$_3$ groups, 2- or 3-thienyl, or 2- or 3-furyl;

Q$_1$ is

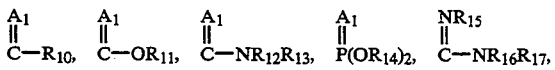

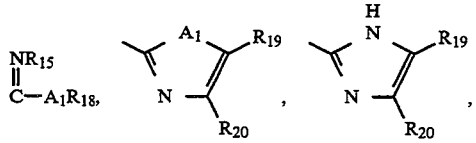

CN,

C$_1$–C$_6$ alkyl optionally substituted with one or more halogen atoms, CN groups or phenyl groups, or phenyl optionally substituted with one or more halogen atoms, C$_1$–C$_4$ alkyl groups, C$_1$–C$_4$ alkoxy groups, CN groups, NO$_2$ groups, CF$_3$ groups or NR$_{21}$R$_{22}$ groups;

A$_1$ is O or S;

R$_{10}$ is C$_1$–C$_6$ alkyl or phenyl;

R$_{11}$ is C$_1$–C$_6$ alkyl;

R$_{12}$ and R$_{13}$ are each independently hydrogen, C$_1$–C$_6$ alkyl or may be taken together with the atom to which they are attached to form a 5- to 7-membered ring;

R$_{14}$ is C$_1$–C$_4$ alkyl;

R$_{15}$ is hydrogen, C$_1$–C$_4$ alkyl or may be taken together with either R$_{16}$ or R$_{18}$ and the atoms to which they are attached to form a 5- to 7-membered ring optionally substituted with one or two C$_1$–C$_4$ alkyl groups;

R$_{16}$ and R$_{17}$ are each independently hydrogen or C$_1$–C$_4$ alkyl;

R$_{18}$ is C$_1$–C$_4$ alkyl or when taken together with R$_{15}$ and the atoms to which they are attached may form a 5- to 7-membered ring optionally substituted with one or two $C_1$-$C_4$ alkyl groups;

$R_{19}$ and $R_{20}$ are each independently hydrogen or $C_1$-$C_4$ alkyl or when taken together may form a ring wherein $R_{19}R_{20}$ is represented by —CH=CH—CH=CH—; and $R_{21}$ and $R_{22}$ are each independently hydrogen or $C_1$-$C_4$ alkyl;

with the proviso that when W is on the 2- or 5-position of the pyrrole ring, then R is other than H.

2. The method according to claim 1 wherein W is

$R_1$ and $R_2$ are each independently hydrogen or $C_1$-$C_4$ alkyl;

X is Q or phenyl optionally substituted with one or more halogen atoms, $NO_2$ groups, CN groups, $C_1$-$C_4$ alkyl groups optionally substituted with one or more halogen atoms, or $C_1$-$C_4$ alkoxy groups optionally substituted with one or more halogen atoms;

Q is

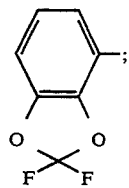

Y is hydrogen, Cl, Br, CN, $NO_2$ or $CF_3$;
Z is hydrogen, Cl, Br or $CF_3$;
R is A or CN;
A is hydrogen,

or $C_1$-$C_6$ alkyl optionally substituted with one to three halogen atoms, one $C_1$-$C_4$ alkoxy group, one cyano, one $C_1$-$C_6$ alkylcarbonyloxy group, one benzylcarbonyloxy group, or one phenylcarbonyloxy group optionally substituted with one to three halogen atoms or one $C_1$-$C_4$ alkyl group; and $R_7$ is phenyl optionally substituted with one or more halogen atoms, $C_1$-$C_4$ alkyl groups, $C_1$-$C_4$ alkoxy groups, CN groups, $NO_2$ groups or $CF_3$ groups.

3. The method according to claim 2 wherein the compound has the structural formula

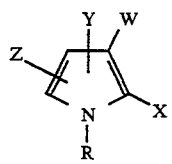

wherein
W is

$R_1$ and $R_2$ are each independently hydrogen or $C_1$-$C_4$ alkyl;

X is Q or phenyl optionally substituted with one or more halogen atoms, $NO_2$ groups, CN groups, $C_1$-$C_4$ alkyl groups optionally substituted with one or more halogen atoms, or $C_1$-$C_4$ alkoxy groups optionally substituted with one or more halogen atoms;

Q is

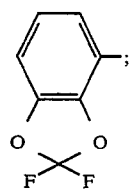

Y is hydrogen, Cl, Br or $CF_3$;
Z is Cl, Br or $CF_3$; and
R is hydrogen or $C_1$-$C_6$ alkyl substituted with one $C_1$-$C_4$ alkoxy group.

4. The method according to claim 2 wherein the compound is selected from the group consisting of 4-cyanopyrrole-2-thiocarboxamide; 4-bromo-2-(p-chlorophenyl)-1-(ethoxymethyl)-5-(trifluoromethyl)pyrrole-3-thiocarboxamide; 4-bromo-2-(p-chlorophenyl)-1-(ethoxymethyl)-N-methyl-5-(trifluoromethyl)pyrrole-3-thiocarboxamide; and 4-(2,3-dichlorophenyl)pyrrole-3-thiocarboxamide.

5. The method according to claim 1 further comprising the simultaneous or sequential addition of an insecticidally or acaricidally effective amount of one or more other biological chemicals.

6. A method for protecting growing plants from attack by insects and acarina which comprises applying to the foliage of said plants or to the soil or water in which they are growing an insecticidally or acaricidally effective amount of a compound having the structural formula

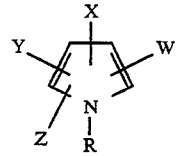

wherein W, X, Y, Z and R are as described in claim 1.

7. The method according to claim 6 wherein W, X, Y, Z and R are as described in claim 2.

8. The method according to claim 6 wherein the compound has the structural formula

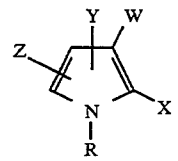

wherein

W is

$R_1$ and $R_2$ are each independently hydrogen or $C_1$–$C_4$ alkyl;

X is Q or phenyl optionally substituted with one or more halogen atoms, $NO_2$ groups, CN groups, $C_1$–$C_4$ alkyl groups optionally substituted with one or more halogen atoms, or $C_1$–$C_4$ alkoxy groups optionally substituted with one or more halogen atoms;

Q is

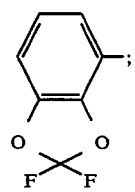

Y is hydrogen, Cl, Br or $CF_3$;
Z is Cl, Br or $CF_3$; and
R is hydrogen or $C_1$–$C_6$ alkyl substituted with one $C_1$–$C_4$ alkoxy group.

9. The method according to claim 7 wherein the compound is selected from the group consisting of 4-cyanopyrrole-2-thiocarboxamide; 4-bromo-2-(p-chlorophenyl)-1-(ethoxymethyl)-5-(trifluoromethyl)pyrrole-3-thiocarboxamide; 4-bromo-2-(p-chlorophenyl)-1-(ethoxymethyl)-N-methyl-5-(trifluoromethyl)pyrrole-3-thiocarboxamide; and 4-(2,3dichlorophenyl)pyrrole-3-thiocarboxamide.

10. The method according to claim 6 wherein the compound is applied to the plants or soil in which they are growing at a rate of about 0.100 kg/ha to 4.0 kg/ha.

* * * * *